United States Patent
Williams

(10) Patent No.: US 10,631,837 B2
(45) Date of Patent: Apr. 28, 2020

(54) ELECTROMECHANICAL SURGICAL APPARATUS INCLUDING WIRE ROUTING CLOCK SPRING

(71) Applicant: Covidien LP, Mansfield, MA (US)

(72) Inventor: Justin Williams, Southbury, CT (US)

(73) Assignee: COVIDIEN LP, Mansfield, MA (US)

( * ) Notice: Subject to any disclaimer, the term of this patent is extended or adjusted under 35 U.S.C. 154(b) by 92 days.

(21) Appl. No.: 15/810,479

(22) Filed: Nov. 13, 2017

(65) Prior Publication Data

US 2018/0064428 A1    Mar. 8, 2018

Related U.S. Application Data

(63) Continuation of application No. 14/535,379, filed on Nov. 7, 2014, now Pat. No. 9,814,450, which is a
(Continued)

(51) Int. Cl.
*A61B 17/00* (2006.01)
*A61B 17/072* (2006.01)
(Continued)

(52) U.S. Cl.
CPC ........ *A61B 17/00* (2013.01); *A61B 17/00234* (2013.01); *A61B 17/07207* (2013.01);
(Continued)

(58) Field of Classification Search
CPC .............. A61B 17/00; A61B 17/00234; A61B 17/0218; A61B 17/0469; A61B 17/068;
(Continued)

(56) References Cited

U.S. PATENT DOCUMENTS 3,123,077 A    3/1964    Alcamo
5,074,863 A    12/1991   Dines
(Continued)

FOREIGN PATENT DOCUMENTS

CN    202211723 U    5/2012
CN    202426578 U    9/2012
(Continued)

OTHER PUBLICATIONS

U.S. Appl. No. 61/661,461, filed Jun. 19, 2012, Williams et al.
(Continued)

*Primary Examiner* — Christopher A Flory

(57) ABSTRACT

An electromechanical surgical system is disclosed including a hand-held surgical instrument, an end effector configured to perform at least one function, and a shaft assembly arranged for selectively interconnecting the end effector and the surgical instrument. The shaft assembly includes a linkage having a proximal housing and a distal housing at least partially received within the proximal housing. The distal housing is rotatable relative to the proximal housing and configured to selectively interconnect the end effector to the shaft assembly. The shaft assembly further includes a wire extending through the linkage having a central portion disposed within an annular groove defined between the proximal and distal housings. The central portion of the wire is annularly wound within the annular groove to define a coil. The coil is configured to at least one of radially expand and contract upon rotation of the distal housing relative to the proximal housing.

20 Claims, 10 Drawing Sheets

Related U.S. Application Data continuation of application No. 13/648,682, filed on Oct. 10, 2012, now Pat. No. 8,906,001.

(51) Int. Cl.
*H01B 7/06* (2006.01)
*H01B 9/00* (2006.01)
*A61B 17/29* (2006.01)
*A61B 90/90* (2016.01)

(52) U.S. Cl.
CPC .............. *H01B 7/065* (2013.01); *H01B 9/003* (2013.01); *A61B 90/90* (2016.02); *A61B 2017/00022* (2013.01); *A61B 2017/00314* (2013.01); *A61B 2017/00398* (2013.01); *A61B 2017/00464* (2013.01); *A61B 2017/00473* (2013.01); *A61B 2017/00482* (2013.01); *A61B 2017/2908* (2013.01); *A61B 2017/2929* (2013.01); *A61B 2017/2931* (2013.01)

(58) Field of Classification Search
CPC ........ A61B 17/07207; A61B 17/12013; A61B 17/1285; A61B 17/29; A61B 17/320016
See application file for complete search history.

(56) References Cited

U.S. PATENT DOCUMENTS

| | | | |
|---|---|---|---|
| 5,098,028 A | 3/1992 | Ida et al. | |
| 5,176,142 A | 1/1993 | Mason | |
| 5,304,071 A | 4/1994 | Bannai et al. | |
| 5,334,023 A | 8/1994 | Schauer et al. | |
| 5,479,929 A | 1/1996 | Cooper et al. | |
| 5,549,637 A | 8/1996 | Crainich | |
| 5,643,294 A | 7/1997 | Tovey et al. | |
| 5,651,687 A | 7/1997 | Du-Rocher et al. | |
| 5,993,454 A | 11/1999 | Longo | |
| 6,434,507 B1 | 8/2002 | Clayton et al. | |
| 6,981,941 B2 | 1/2006 | Whitman et al. | |
| 7,081,001 B1 | 7/2006 | Conroy et al. | |
| 7,189,247 B1* | 3/2007 | Zirps | A61B 1/00087 606/140 |
| 7,717,312 B2 | 5/2010 | Beetel | |
| 7,918,376 B1 | 4/2011 | Knodel et al. | |
| 7,951,071 B2 | 5/2011 | Whitman et al. | |
| 8,020,742 B2 | 9/2011 | Marczyk | |
| 8,033,441 B2 | 10/2011 | Marczyk | |
| 8,092,493 B2 | 1/2012 | Marczyk | |
| 8,322,483 B2 | 12/2012 | Sy et al. | |
| 8,568,425 B2 | 10/2013 | Ross et al. | |
| 8,657,177 B2 | 2/2014 | Scirica et al. | |
| 8,727,539 B2 | 5/2014 | Todoroki | |
| 8,899,462 B2 | 12/2014 | Kostrzewski et al. | |
| 8,906,001 B2 | 12/2014 | Williams | |
| 9,814,450 B2 | 11/2017 | Williams | |
| 2003/0014077 A1 | 1/2003 | Leung et al. | |
| 2003/0216716 A1 | 11/2003 | Desarzens | |
| 2003/0233104 A1 | 12/2003 | Gellman et al. | |
| 2004/0010245 A1 | 1/2004 | Cerier et al. | |
| 2004/0034369 A1 | 2/2004 | Sauer et al. | |
| 2004/0082850 A1* | 4/2004 | Bonner | A61B 5/06 600/424 |
| 2004/0153124 A1 | 8/2004 | Whitman | |
| 2004/0250959 A1 | 12/2004 | Mok et al. | |
| 2005/0256533 A1 | 11/2005 | Roth et al. | |
| 2006/0036232 A1 | 2/2006 | Primavera et al. | |
| 2006/0111209 A1 | 5/2006 | Hinman et al. | |
| 2006/0142656 A1 | 6/2006 | Malackowski et al. | |
| 2008/0109012 A1 | 5/2008 | Falco et al. | |
| 2008/0214967 A1 | 9/2008 | Aranyi | |
| 2008/0255413 A1 | 10/2008 | Zemlok et al. | |
| 2008/0255607 A1 | 10/2008 | Zemlok | |
| 2008/0262654 A1 | 10/2008 | Omori et al. | |
| 2008/0272172 A1 | 11/2008 | Zemlok et al. | |
| 2009/0090763 A1 | 4/2009 | Zemlok et al. | |
| 2009/0134199 A1 | 5/2009 | Heinrich et al. | |
| 2009/0312773 A1 | 12/2009 | Cabrera et al. | |
| 2010/0001036 A1 | 1/2010 | Marczyk et al. | |
| 2010/0012702 A1 | 1/2010 | Marczyk | |
| 2010/0200636 A1 | 8/2010 | Zemlok et al. | |
| 2010/0211053 A1 | 8/2010 | Ross et al. | |
| 2010/0312257 A1 | 12/2010 | Aranyi | |
| 2010/0320254 A1 | 12/2010 | Zemlok et al. | |
| 2011/0017801 A1 | 1/2011 | Zemlok et al. | |
| 2011/0022032 A1 | 1/2011 | Zemlok et al. | |
| 2011/0034910 A1 | 2/2011 | Ross et al. | |
| 2011/0036892 A1 | 2/2011 | Marczyk et al. | |
| 2011/0062211 A1 | 3/2011 | Ross et al. | |
| 2011/0079626 A1 | 4/2011 | Viola et al. | |
| 2011/0082484 A1 | 4/2011 | Saravia et al. | |
| 2011/0106073 A1 | 5/2011 | Mueller | |
| 2011/0121049 A1 | 5/2011 | Malinouskas et al. | |
| 2011/0168757 A1 | 7/2011 | Viola et al. | |
| 2011/0172681 A1 | 7/2011 | Aranyi et al. | |
| 2011/0174099 A1 | 7/2011 | Ross et al. | |
| 2011/0190738 A1 | 8/2011 | Zemlok et al. | |
| 2011/0278344 A1 | 11/2011 | Zemlok et al. | |
| 2011/0295242 A1* | 12/2011 | Spivey | A61B 17/07207 606/1 |
| 2011/0313405 A1 | 12/2011 | Anderson et al. | |
| 2012/0089131 A1 | 4/2012 | Zemlok et al. | |
| 2012/0109154 A1 | 5/2012 | Ross et al. | |
| 2012/0116261 A1 | 5/2012 | Mumaw et al. | |
| 2012/0116363 A1 | 5/2012 | Houser et al. | |
| 2012/0129409 A1 | 5/2012 | Drew et al. | |
| 2013/0023923 A1* | 1/2013 | Mueller | A61B 17/29 606/205 |
| 2013/0098965 A1 | 4/2013 | Kostrzewski et al. | |
| 2013/0123783 A1 | 5/2013 | Marczyk et al. | |
| 2013/0237986 A1* | 9/2013 | Mueller | A61B 17/29 606/52 |
| 2014/0155886 A1* | 6/2014 | Mueller | A61B 17/29 606/41 |
| 2014/0291383 A1* | 10/2014 | Spivey | A61B 17/07207 227/177.1 |
| 2014/0371630 A1* | 12/2014 | Roe | G01N 25/72 600/583 |
| 2015/0148754 A1* | 5/2015 | Eich | A61M 5/20 604/235 |

FOREIGN PATENT DOCUMENTS

| | | |
|---|---|---|
| DE | 4423881 C1 | 10/1995 |
| EP | 1736112 A1 | 12/2006 |
| EP | 1782738 A2 | 5/2007 |
| EP | 2027819 A1 | 2/2009 |
| EP | 2316366 A2 | 5/2011 |
| EP | 2446835 A1 | 5/2012 |
| JP | 201178227 A | 4/2011 |
| JP | 201192743 A | 5/2011 |
| WO | 9811829 A1 | 3/1998 |
| WO | 2004107989 A1 | 12/2004 |
| WO | 2007026354 A1 | 3/2007 |
| WO | 2008131362 A2 | 10/2008 |
| WO | 2008133956 A2 | 11/2008 |
| WO | 2009039506 A1 | 3/2009 |

OTHER PUBLICATIONS

U.S. Appl. No. 61/673,792, filed Jul. 20, 2012, Williams et al.
Canadian Office Action dated Jul. 15, 2019 corresponding to counterpart Patent Application CA 2,828,562.

\* cited by examiner

ELECTROMECHANICAL SURGICAL APPARATUS INCLUDING WIRE ROUTING CLOCK SPRING

CROSS-REFERENCE TO RELATED APPLICATIONS

This application is a continuation of U.S. application Ser. No. 14/535,379, filed Nov. 7, 2014, which is a continuation of U.S. patent application Ser. No. 13/648,682 filed Oct. 10, 2012, (now U.S. Pat. No. 8,906,001) and the disclosure of the above-identified application are hereby incorporated by reference in its entirety.

BACKGROUND

1. Technical Field

The present disclosure relates to surgical apparatus, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating electromechanical surgical devices. In many instances the electromechanical surgical devices include a reusable handle assembly, and a plurality of disposable or single use end effectors, commonly called single use loading units (SULU). An end effector is selectively connected to the handle assembly prior to use and then disconnected from the handle assembly following use in order to be disposed of or in some instances sterilized for re-use.

In some instances, end effectors having different operational properties and parameters may be attached to the same reusable handle assembly to facilitate use of the reusable handle assembly in a large variety of surgical procedures. It is important, however, to match the output properties of the drive system of the reusable handle assembly to the operational properties and parameters of the currently attached end effector. Thus, there is a need for an identification system that identifies the end effector to the reusable handle assembly without impeding the operational properties and parameters of the end effector.

SUMMARY

Further details and aspects of exemplary embodiments of the present invention are described in more detail below with reference to the appended Figures.

An electromechanical surgical system is disclosed including a hand-held surgical instrument, an end effector configured to perform at least one function, and a shaft assembly arranged for selectively interconnecting the end effector and the surgical instrument. The shaft assembly includes a linkage having a proximal housing and a distal housing at least partially received within the proximal housing. The distal housing is rotatable relative to the proximal housing and configured to selectively interconnect the end effector to the shaft assembly. The shaft assembly further includes a wire extending through the linkage. The wire includes a central portion disposed within an annular groove defined between the proximal and distal housings. The central portion of the wire is annularly wound within the annular groove to define a coil. The coil is configured to at least one of radially expand and contract upon rotation of the distal housing relative to the proximal housing.

In an aspect of the present disclosure, the proximal housing includes an outer housing and an inner housing and the inner housing is configured for reception within the outer housing.

In an aspect of the present disclosure, each of the inner and outer housings includes an opening extending therethrough for the reception of a proximal portion of the wire.

In an aspect of the present disclosure, the openings of the inner and outer housings are substantially aligned.

In an aspect of the present disclosure, the inner housing includes an annular lip and an outer wall and the annular groove extends between the annular lip and the outer wall.

In an aspect of the present disclosure, the inner and outer housings define at least one chamber therebetween for the reception of at least one gear therein.

In an aspect of the present disclosure, the distal housing includes an opening extending therethrough for the reception of a distal portion of the wire.

In an aspect of the present disclosure, the central portion of the coil is configured to radially expand when the distal housing is rotated relative to the proximal housing in a first direction and to radially contract when the distal housing is rotated relative to the proximal housing in a second direction.

In an aspect of the present disclosure, the wire is disposed in electrical communication with the surgical instrument and the end effector and is configured to communicate information between the surgical instrument and the end effector.

In an aspect of the present disclosure, the central portion of the coil of the wire is annularly wound within the annular groove in a single plane.

A surgical system is disclosed including a hand-held surgical instrument, an end effector configured to perform at least one function, and a shaft assembly arranged for selectively interconnecting the end effector and the surgical instrument. The shaft assembly includes a linkage defining a longitudinal axis and having a proximal housing and a distal housing at least partially received within the proximal housing. The distal housing is rotatable relative to the proximal housing and configured to selectively interconnect the end effector to the shaft assembly. The shaft assembly further includes a wire extending through the linkage. The wire includes a proximal portion extending through the proximal housing, a central portion disposed within an annular groove defined between the proximal and distal housings, and a distal portion extending through the distal housing. The central portion of the wire is annularly wound within the annular groove to define a coil. The coil is configured to radially at least one of expand and contract upon rotation of the distal housing relative to the proximal housing. The proximal and distal portions of the wire are substantially longitudinally fixed relative to the proximal and distal housings.

In an aspect of the present disclosure, the distal housing is rotatable relative to the proximal housing in a first direction between a first configuration and at least a second configuration, and rotatable relative to the proximal housing in a second direction between the first configuration and at least a third configuration.

In an aspect of the present disclosure, the distal housing is rotatable relative to the proximal housing between about 0° and at least about 180° from the first configuration in the first direction to achieve the second configuration and between about 0° and at least about 180° from the first configuration in the second direction to achieve the third configuration.

In an aspect of the present disclosure, the end effector is rotatably fixed to the distal housing and rotatable relative to the shaft assembly between about 0° and at least about 180° in either direction upon rotation of the distal housing relative to the proximal housing.

In an aspect of the present disclosure, the coil of the wire is configured to radially expand when the distal housing is rotated in the first direction relative to the proximal housing and radially contract when the distal housing is rotated in the second direction relative to the proximal housing.

In an aspect of the present disclosure, the proximal portion of the wire is disposed in electrical communication with the surgical instrument and the distal portion of the wire is disposed in electrical communication with the end effector.

In an aspect of the present disclosure, the wire is configured to communicate information between the end effector and the surgical instrument.

A wire routing assembly for use with a surgical system is disclosed including a linkage assembly for operatively interconnecting an end effector to a surgical instrument. The linkage assembly includes a proximal housing and a distal housing at least partially received within the proximal housing and rotatable relative to the proximal housing. The wire routing assembly further includes a wire extending through the linkage assembly and having a central portion disposed within an annular groove defined between the proximal and distal housings. The central portion of the wire is annularly wound within the annular groove to define a coil, the coil being configured to radially expand and contract upon rotation of the distal housing relative to the proximal housing.

In an aspect of the present disclosure, the coil of the wire is configured to radially expand when the distal housing is rotated relative to the proximal housing in a first direction and to radially contract when the distal housing is rotated relative to the proximal housing in a second direction.

In an aspect of the present disclosure, the coil of the wire is annularly wound within the annular groove in a single plane.

In an aspect of the present disclosure, the wire is disposed in electrical communication with the surgical instrument and the end effector. The wire is configured to communicate information between the surgical instrument and the end effector.

It is contemplated that any of the above disclosed aspects may be combined without departing from the scope of the present disclosure.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
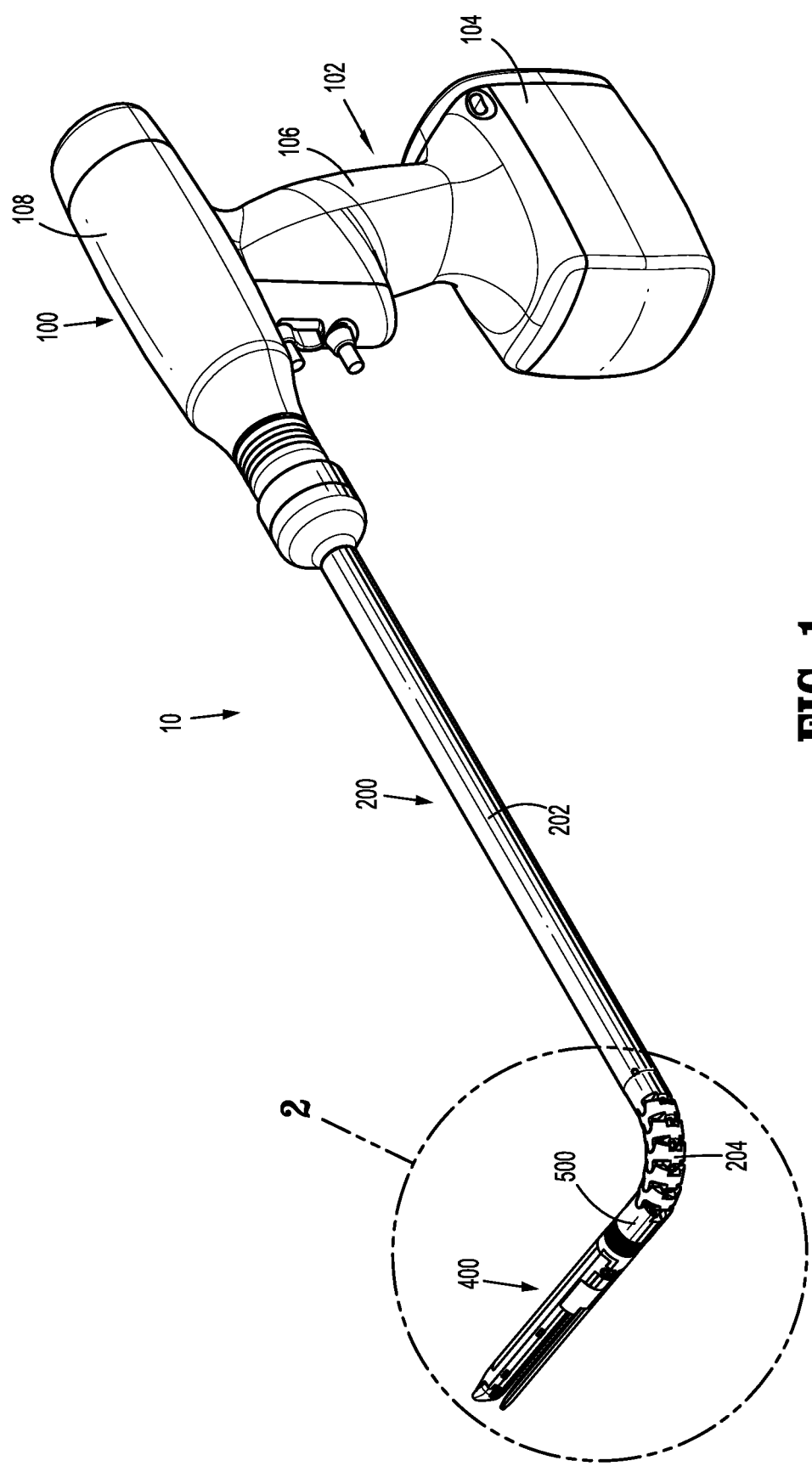
FIG. 1 is a perspective view of an electromechanical surgical system according to the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user.

Referring initially to FIG. 1, an electromechanical, handheld, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 400, via a shaft assembly 200. The end effector 400 and the shaft assembly 200 are each configured for actuation and manipulation by the electromechanical, hand-held, powered surgical instrument 100. In particular, surgical instrument 100 is configured for selective connection with shaft assembly 200, and, in turn, shaft assembly 200 is configured for selective connection with any one of a plurality of different end effectors 400.

Figure 2:
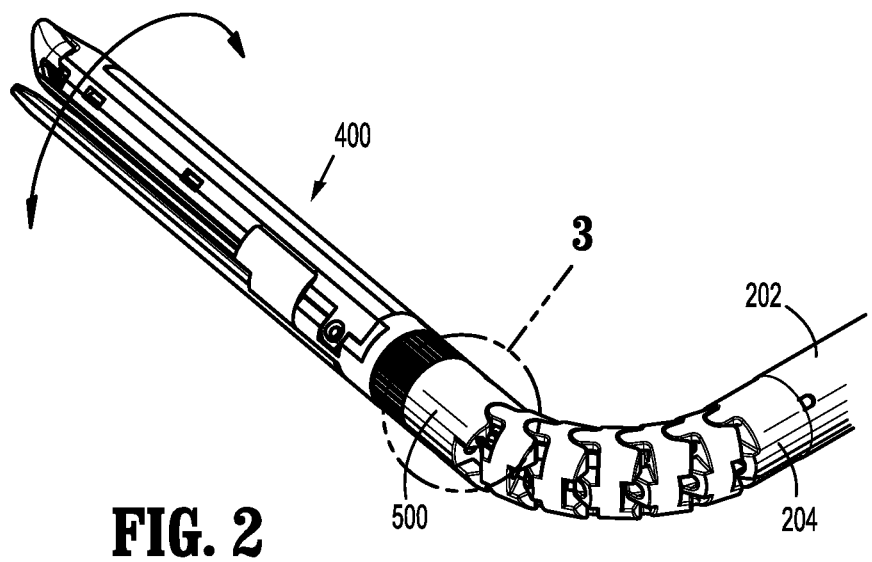
FIG. 2 is a perspective view of the area of detail of FIG. 1, illustrating a shaft assembly and an end effector of the surgical system of FIG. 1.
Figure 3:
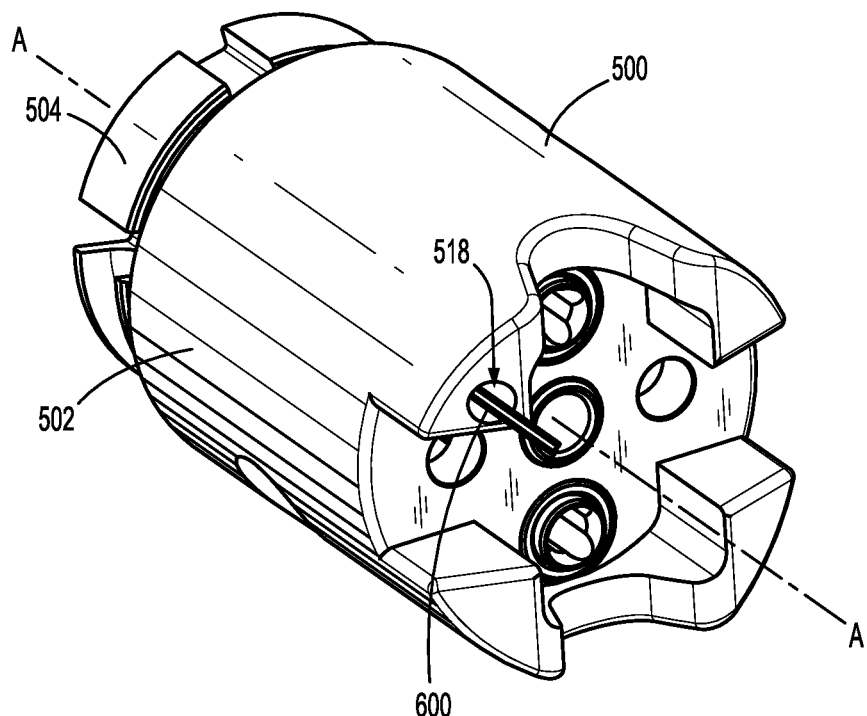
FIG. 3 is a distal perspective view of the area of detail of FIG. 2, illustrating a linkage of the shaft assembly of FIG. 2.

Referring now to FIGS. 1 and 2, surgical instrument 100 includes an instrument housing 102 having a lower housing portion 104, an intermediate housing portion 106 extending from and/or supported on lower housing portion 104, and an upper housing portion 108 extending from and/or supported on intermediate housing portion 106.

The shaft assembly 200 includes an elongate portion 202 configured for selective connection to upper housing portion 108 of instrument housing 102, a flexible portion 204 extending from the elongate portion 202, and a linkage 500 extending from the flexible portion 204 and configured to selectively connect the shaft assembly 200 to a plurality of different end effectors 400.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which being hereby incorporated herein by reference, for a detailed description of the construction and operation of exemplary electromechanical, hand-held, powered surgical instrument 100.

Reference may also be made to provisional patent application No. 61/661,461, Filed Jun. 19, 2012, and H-US-03447 (203-8880), entitled "APPARATUS FOR ENDOSCOPIC PROCEDURES," provisional patent application No. 61/673,792, filed Jul. 20, 2012, the entire contents of each of which being incorporated herein by reference, for a detailed description of the construction and operation of an exemplary shaft assembly 200 and end effector 400 for use with the electromechanical, hand-held, powered surgical instrument 100.

End effector 400 can be a variety of surgical end effectors, such as, for example, a linear surgical stapling end effector, as shown in FIG. 1. Such linear surgical stapling end effector includes a staple cartridge, anvil member, and drive member for driving staples out of the staple cartridge and against the anvil member. Such an instrument is disclosed in U.S. patent application Ser. No. 13/280,859, Ser. No. 13/280,880, and Ser. No. 13/280,898, the entire disclosures of which are hereby incorporated by reference herein. For example, the drive member can be threadedly engaged with a threaded screw, the threaded screw being driven by one or more gears of the linkage 500, rotation being transmitted therethrough from the shaft assembly 200. Rotation of such threaded screw can be made to move the drive member longitudinally through the staple cartridge to fire the staples. Other types of end effectors are contemplated including, but not limited to, electrosurgical end effectors that apply electrical energy to tissue and/or ultrasonic end effectors that apply ultrasonic energy to tissue.

Referring now to FIGS. 3-8, linkage 500 includes a proximal housing assembly 502 and a distal housing assembly 504. Proximal housing assembly 502 includes an outer housing 506 and an inner housing 508. Outer housing 506 is configured to receive inner housing 508 such that inner shelves or ledges 510 (FIG. 6) of outer housing 506 are received within recesses 512 (FIG. 6) of inner housing 508. In this manner inner housing 508 is rotatably fixed relative to outer housing 506. Outer housing 506 and inner housing 508 together define first, second and third recesses or chambers 514a-514c (FIG. 8) for the reception of drive gears 516a-516c therein. For example, first chamber 514a receives a first gear 516a therein, second chamber 514b receives a second gear 516b therein, and third chamber 514c receives a third gear 516c therein. Each of gears 516a-516c is operatively associated with surgical instrument 100 and configured for actuation and manipulation by surgical instrument 100.

Figure 6:
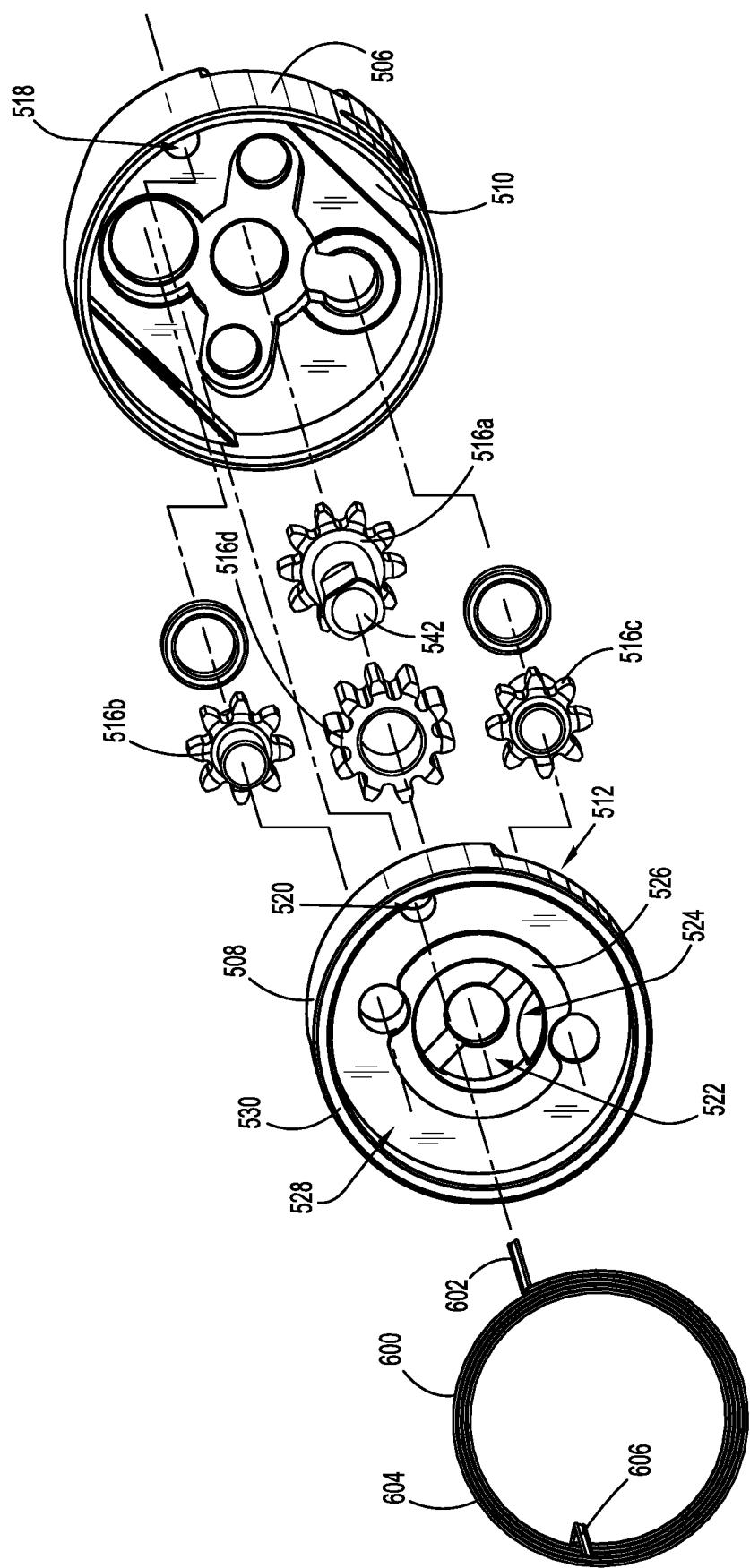
FIG. 6 is a perspective view, with parts separated, of the proximal housing of FIG. 5.

As seen in FIG. 6, outer housing 506 includes a first opening 518 extending therethrough and inner housing 508 includes a second opening 520 extending therethrough. First and second openings 518 and 520 are substantially aligned when inner housing 510 is received within outer housing 508 and are configured for the reception of a wire 600 therethrough.

With continued reference to FIG. 6, inner housing 508 includes a central recess 522 located on a distal side thereof configured for reception of a fourth gear 516d therein. Central recess 522 includes a radial opening 524 configured to allow for engagement between gear 516d and gear 516c. Inner housing 508 also includes an annular lip 526 disposed about central recess 522 and defines an annular groove 528 between annular lip 526 and an outer wall 530 of inner housing 508 for the receipt of wire 600 therein and therearound.

Figure 5:
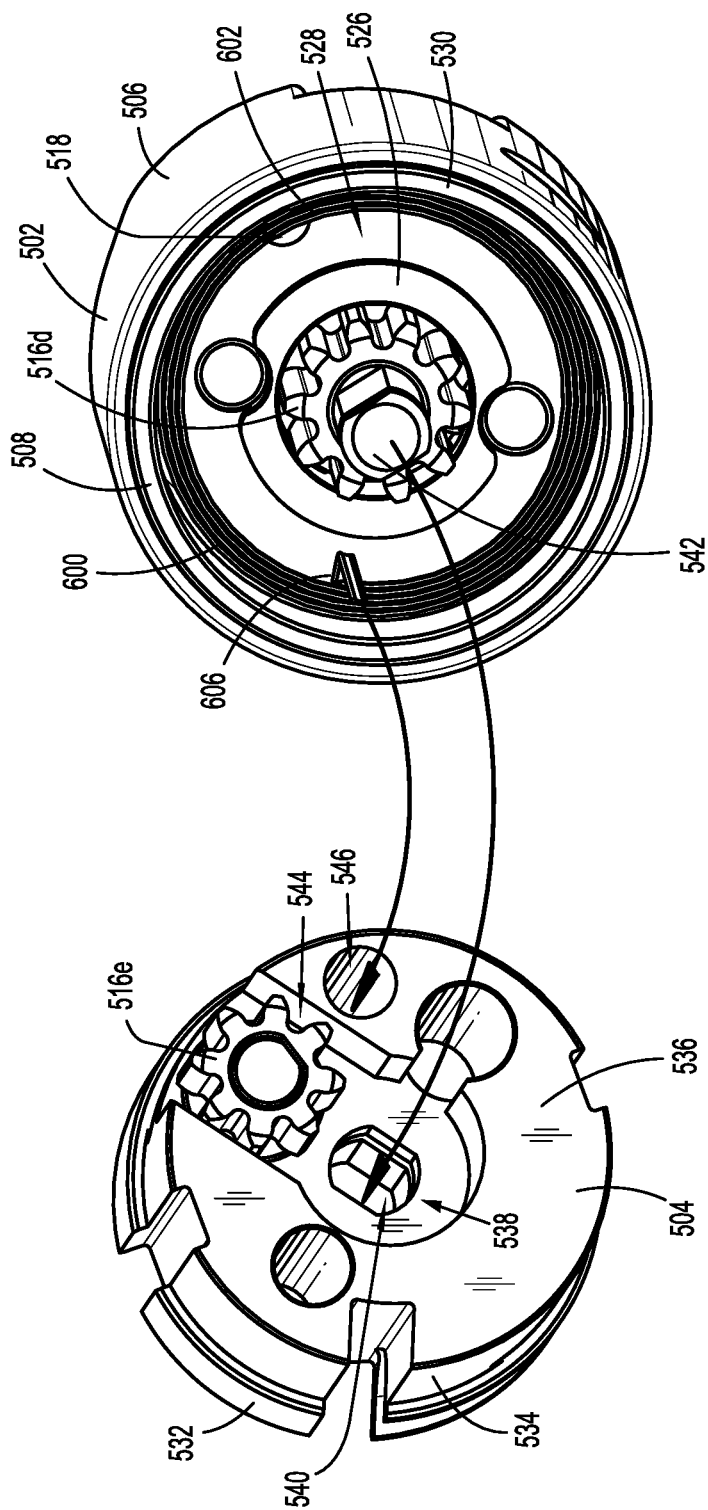
FIG. 5 is a perspective view of the linkage of FIGS. 3 and 4, illustrating a distal housing detached from a proximal housing of the linkage.
Figure 7:
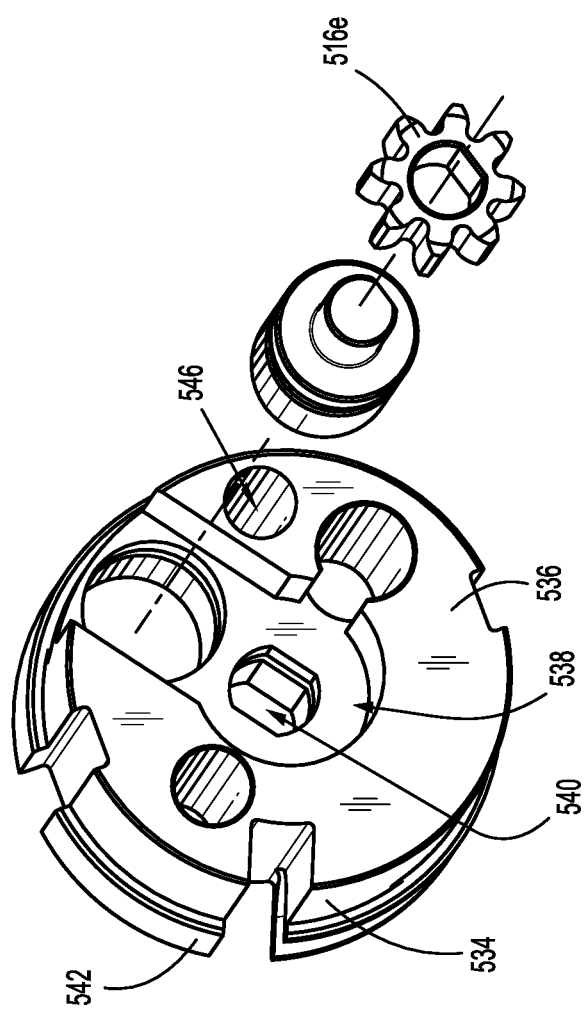
FIG. 7 is a perspective view, with parts separated, of the distal housing of FIG. 5.
Figure 8:
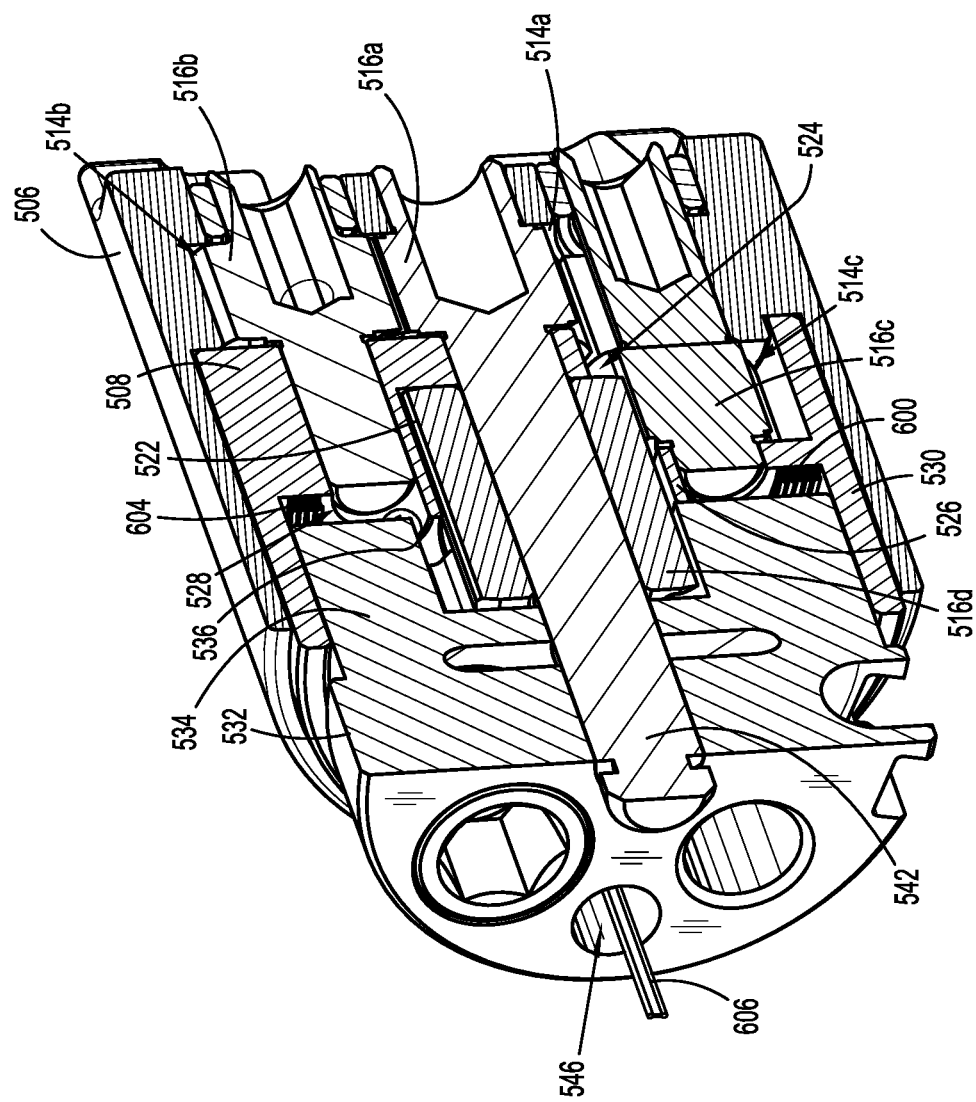
FIG. 8 is a side, perspective, cross-sectional view of the linkage of FIGS. 3 and 4, as taken along section line 8-8 of FIG. 4.

Referring now to FIGS. 5, 7 and 8, distal housing assembly 504 includes a flanged portion 532 at a distal end and a recessed portion 534 extending proximally from the flanged portion 532. Recessed portion 534 is configured for rotatable reception in inner housing 508 such that a proximal end 536 of recessed portion 534 abuts or is adjacent annular lip 526. Recessed portion 534 includes a central cut-out or recess 538 configured to receive a portion of gear 516d therein and a slot 540 extending through central cut-out 538 and configured to receive a shaft 542 of gear 516a therein. Distal housing assembly 504 includes a gear 516e disposed in a radial channel 544 extending through recessed portion 534 and configured for engagement with a distal portion of gear 516d. When recessed portion 534 of distal housing assembly 504 is inserted into inner housing 508, annular groove 528 defines a cavity between distal housing assembly 504 and inner housing 508 for the reception of wire 600 therein and therearound. Distal housing assembly 504 also includes a third opening 546 extending therethrough for the reception of wire 600.

Thus, the gears are provided to drive various functions of the end effector 400. The gears 516a through 516e form two inputs: one that drives the threaded screw, and one that drives rotation of the end effector with respect to the shaft assembly 200. Gear 516c is a firing gear that drives idler gear 516d, which drives an output gear 516e. Gear 516e is attached to a hexagonal drive that attaches to the threaded screw. There is also a rotation drive gear 516a that is keyed to part of the linkage housing 532 so that when gear 516b is driven, it rotates housing 504. Other gearing arrangements are contemplated.

Figure 4:
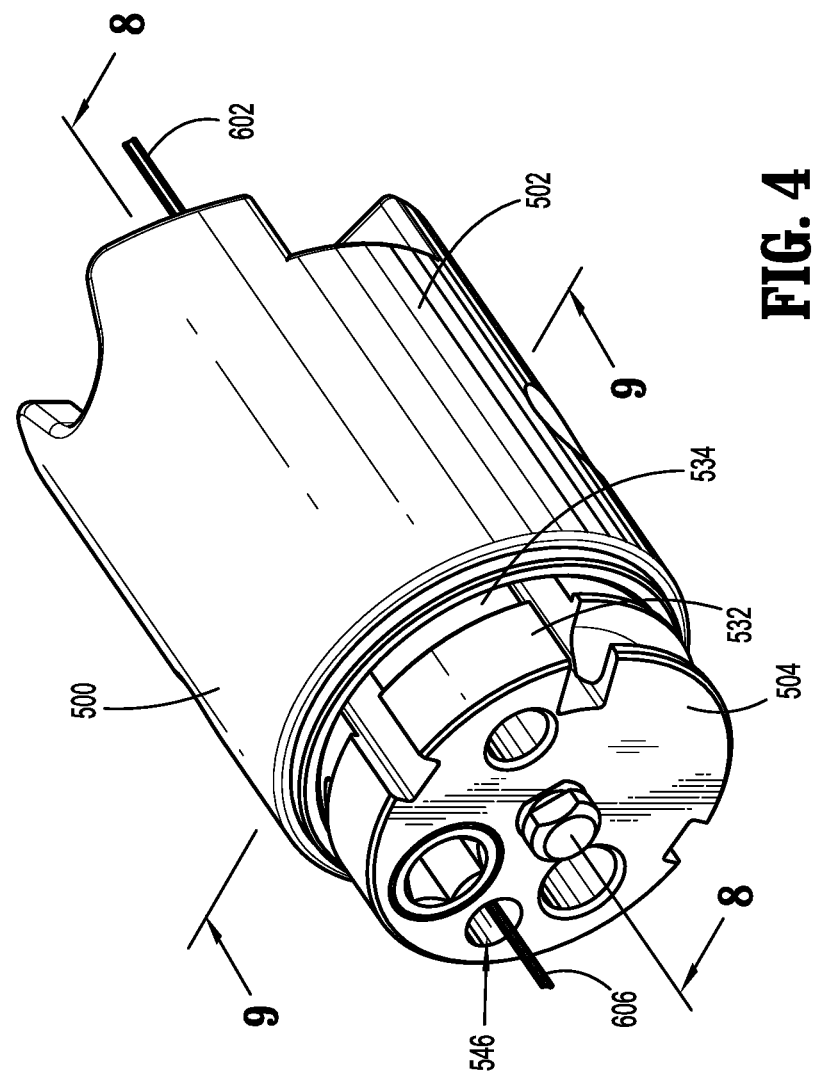
FIG. 4 is a proximal perspective view of the area of detail of FIG. 2, illustrating a linkage of the shaft assembly of FIG. 2.
Figure 4A:
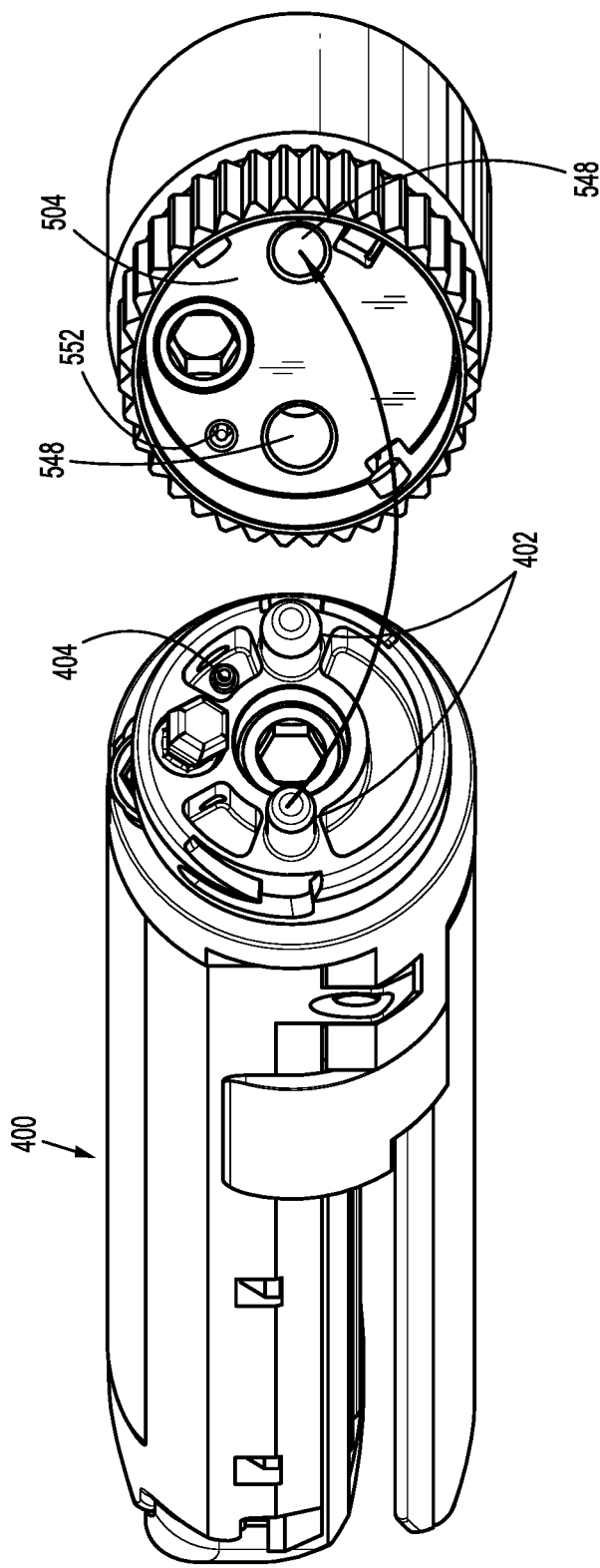
FIG. 4A is a perspective view of the end effector and the linkage assembly of the electromechanical surgical system of FIG. 1, illustrating the end effector detached form the distal housing assembly.

Referring now to FIG. 4A, distal housing assembly 504 includes a pair of openings 548 configured to receive a pair of tabs 402 of end effector 400 when end effector 400 is attached thereto. Tabs 402 and openings 548 inhibit rotation of end effector 400 relative to distal housing assembly 504 such that end effector 400 and distal housing assembly 504 are configured to rotate together relative to proximal housing assembly 502 and shaft assembly 200.

End effector 400 may also include a plug interface 404 configured to electrically engage wire 600 (FIG. 4) when end effector 400 is attached to distal housing assembly 504 and electrically communicate end effector 400 with wire 600 and surgical instrument 100. Distal housing assembly 504 may also include a plug interface 552 for electrical engagement with plug interface 404 of end effector 400 where wire 600 (FIG. 4) is electrically connected to plug interface 552 instead of plug interface 404.

Figure 12:
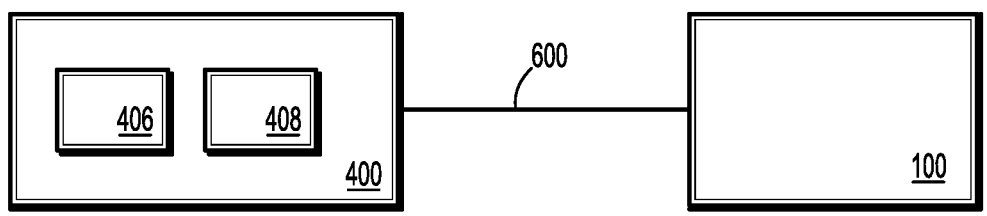
FIG. 12 is a schematic diagram of the electrical connection between an end effector and a surgical instrument of the electromechanical surgical system of FIG. 1.

Referring now to FIGS. 6, 8 and 12, wire 600 includes a proximal portion 602, a central portion 604 and a distal portion 606. Central portion 604 of wire 600 is disposed within annular groove 528 between inner housing 508 and distal housing assembly 504 and is annularly wound about annular lip 526 in the fashion of a clock spring or coil. For example, central portion 604 of wire 600 may be wound radially within annular groove 528 in a single plane such that each successive winding of wire 600 is disposed radially adjacent to an immediately prior winding. Proximal portion 602 of wire 600 extends from central portion 604 through the second opening 520 of inner housing 508 to electrically communicate with surgical instrument 100. Distal portion 606 of wire 600 extends through the third opening 546 to electrically communicate with end effector 400. In this manner, end effector 400 is in electrical communication with surgical instrument 100 via wire 600. Proximal and distal portions 602, 606 of wire 600 may be substantially longitudinally fixed within the proximal and distal housings 502, 504, respectively.

Wire 600 is configured to transmit information from the end effector 400 to the surgical instrument 100. For example, wire 600 may be an electrical wire configured to transmit an identification signal from a memory chip 406 (FIG. 12) of end effector 400 to surgical instrument 100, e.g. an E-prom signal, to identify the type of end effector 400 to surgical instrument 100. The output properties of the drive system of the surgical instrument 100 may then be matched to the operational properties and parameters of the particular identified end effector 400. It is also contemplated that wire 600 may transmit a signal containing other kinds of information including, for example, information about the target tissue (e.g., tissue type, tissue vascularity, tissue temperature, etc.) sensed by sensors 408 (FIG. 12) of the end effector 400, a status of the operative state of the end effector 400, or other similar operational information. For example, an E-prom signal may be transmitted along wire 600 to surgical instrument 100 when the end effector 400 has been at least partially fired, when the end effector 400 has been at least partially clamped to target tissue, or other similar operational parameters.

During use of surgical instrument 100 and end effector 400, it may be desirable to rotate end effector 400 about a longitudinal axis thereof in either a clockwise or a counter clockwise direction. In view thereof, wire 600 is capable of communicating information between surgical instrument 100 and end effector 400 irrespective of the rotational orientation of end effector 400 relative to surgical instrument 100.

Figure 9:
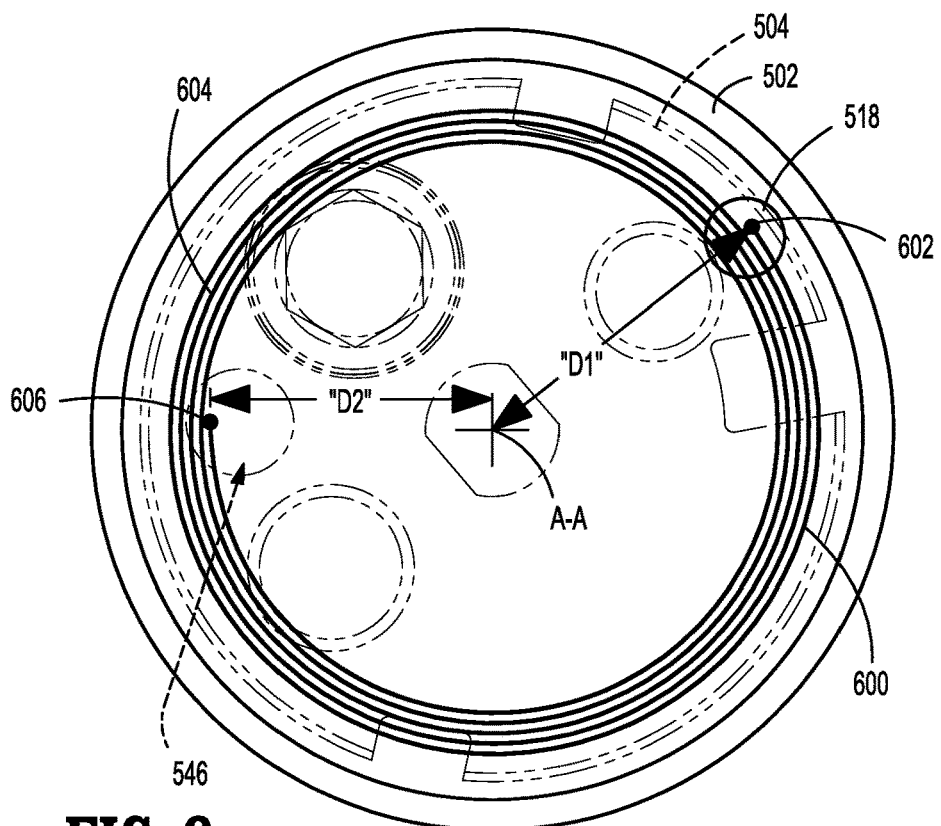
FIGS. 9-11 are cross-sectional views taken along section line 9-9 of FIG. 4, illustrating the distal housing and the proximal housing in various rotational configurations.

Referring initially to FIG. 9, wire 600 is disposed in a first configuration prior to rotation of distal housing assembly 504 relative to proximal housing assembly 502 (i.e., rotation of end effector 400 relative to shaft assembly 200 and/or surgical instrument 100). Proximal portion 602 of wire 600 is disposed a first radial distance "D1" from longitudinal axis A-A, and distal portion 606 of wire 600 is disposed a second radial distance "D2" from longitudinal axis A-A and central portion 604 is coiled about annular groove 528 between the first and second radial distances "D1" and "D2".

Figure 10:
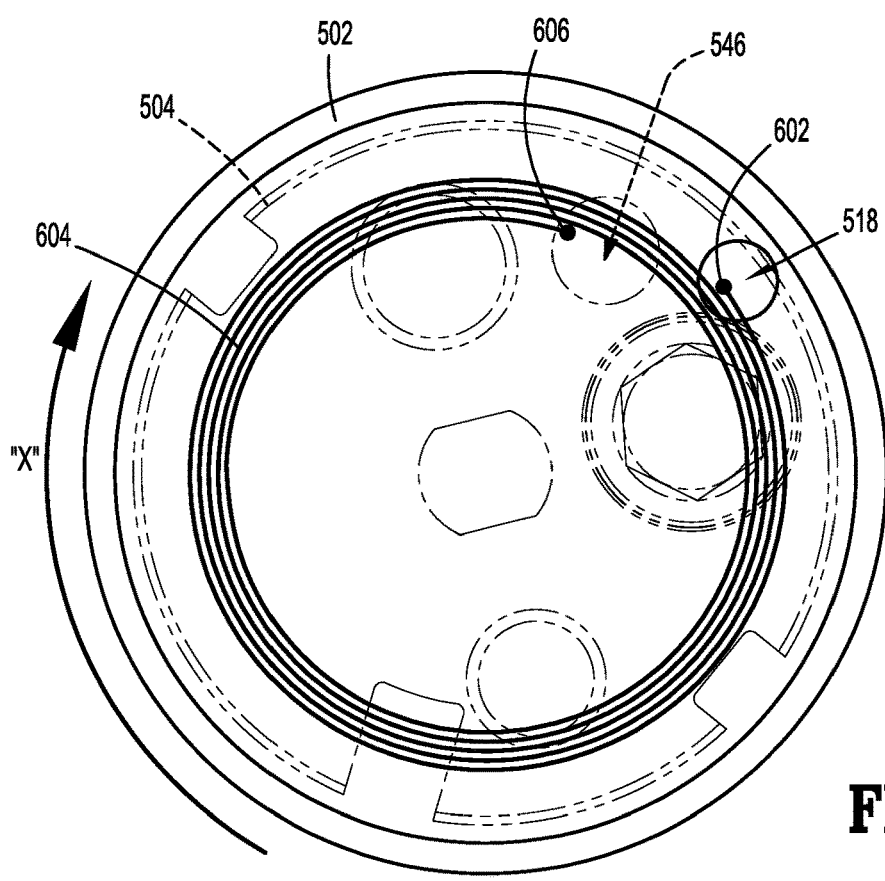

Referring now to FIG. 10, when end effector 400 is rotated relative to shaft assembly 200 and/or surgical instrument 100, in a clockwise direction as depicted in FIG. 10, causing distal housing assembly 504 to be rotated in the direction "X", third opening 546 of distal housing assembly 504 is rotated in the direction "X". As third opening 546 rotates in the direction "X", a side of third opening 546 engages distal portion 606 of wire 600 and also rotates distal portion 606 in the direction "X". As distal portion 606 of wire 600 rotates in the direction "X", central portion or coil 604 of wire 600 is radially contracted or constricted to a second configuration, similar to winding up a clock or coil spring. In other words, wire 600 has been wound up.

It is contemplated that distal housing assembly 504 may be rotated in the direction "X" between about a 0° rotation and at least about a 180° rotation relative to the first configuration. It is also contemplated that housing assembly 504 may be rotated in the direction "X" more than about a 180° rotation and, for example, may rotate through more than about one full 360° rotation relative to the first configuration.

Figure 11:
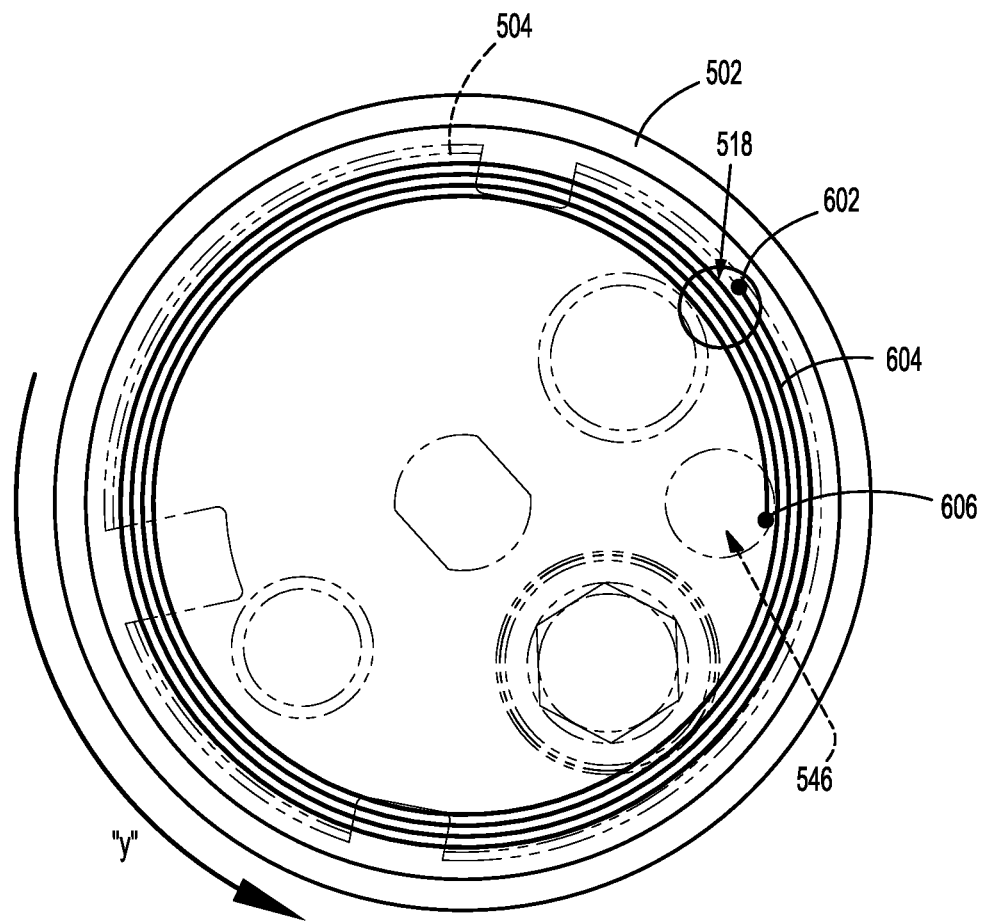

Referring now to FIG. 11, when end effector 400 is rotated relative to shaft assembly 200 and/or surgical instrument 100, in a counter-clockwise direction as depicted in FIG. 11, causing distal housing assembly 504 to be rotated in the direction "Y", third opening 546 of distal housing assembly 504 is rotated in the direction "Y". As third opening 546 rotates in the direction "Y", a side of third opening 546 engages distal portion 606 of wire 600 and also rotates distal portion 606 in the direction "Y". As distal portion 606 of wire 600 rotates in the direction "Y", central portion or coil 604 of wire 600 is radially expanded, similar to un-winding a clock spring. In other words, wire 600 has been un-wound.

It is contemplated that distal housing assembly 504 may be rotated in the direction "Y" between about a 0° rotation and at least about a 180° rotation relative to the first configuration. It is also contemplated that housing assembly 504 may be rotated in the direction "Y" more than about a 180° rotation and, for example, may rotate through more than about one full 360° rotation relative to the first configuration.

In this manner, linkage 500 provides a wire routing that allows end effector 400 to be rotated about axis A-A without wire 600 becoming tangled or without wire 600 inhibiting the rotation. It is contemplated that central portion or coil 604 of wire 600 may alternatively radially expand when distal housing assembly is rotated in the direction "X" and radially contract when distal housing assembly is rotated in the direction "Y" (Opposite direction "X").

It is contemplated that proximal portion 602 of wire 600 may have substantially the same radial distance from longitudinal axis A-A in each of the first, second and third configurations. Likewise, it is contemplated that distal portion 606 of wire 600 may have substantially the same radial distance from longitudinal axis A-A in each of the first, second and third configurations.

Alternatively, it is contemplated that the radial distance of proximal portion 602 from longitudinal axis A-A in the second configuration may be smaller than the radial distance of proximal portion 602 from longitudinal axis A-A in the first configuration, and that the radial distance of proximal portion 602 from longitudinal axis A-A in the third configuration may be larger than the radial distance of proximal portion 602 from longitudinal axis A-A in the first configuration. Likewise, it is contemplated that the radial distance of distal portion 606 from longitudinal axis A-A in the second configuration may be smaller than the radial distance of distal portion 606 from longitudinal axis A-A in the first configuration, and that the radial distance of distal portion 606 from longitudinal axis A-A in the third configuration may be larger than the radial distance of distal portion 606 from longitudinal axis A-A in the first configuration.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

The invention claimed is:
1. An electromechanical surgical system, comprising:
 a shaft assembly including an elongate portion and a linkage extending along a longitudinal axis, the linkage including:
  a proximal housing assembly;

a distal housing assembly partially received within the proximal housing assembly and rotatable relative to the proximal housing assembly about the longitudinal axis;

a gear disposed within a recess defined in the proximal housing assembly; and a wire including a proximal portion coupled to the proximal housing assembly, a distal portion coupled to the distal housing assembly, and a central portion wound radially around the longitudinal axis within an annular groove defined between the proximal and distal housing assemblies, the central portion lying in a single plane with each successive winding of the wire disposed radially adjacent to an immediately prior winding.

2. The electromechanical system according to claim 1, wherein the proximal portion of the wire is longitudinally fixed within the proximal housing assembly and the distal portion of the wire is longitudinally fixed within the distal housing assembly.

3. The electromechanical system according to claim 1, wherein when the wire is disposed in a first configuration, prior to rotation of the distal housing assembly relative to the proximal housing assembly:

the proximal portion of the wire is disposed at a first radial distance from the longitudinal axis;

the distal portion of the wire is disposed at a second radial distance from the longitudinal axis, and the central portion of the wire is coiled within the annular groove between the first and second radial distances.

4. The electromechanical system according to claim 1, wherein rotation of the distal housing assembly in a first direction relative to the proximal housing assembly causes the distal portion of the wire to rotate in the first direction such that the central portion of the wire radially contracts within the annular groove.

5. The electromechanical system according to claim 4, wherein rotation of the distal housing assembly in a second direction relative to the proximal housing assembly causes the distal portion of the wire to rotate in the second direction such that the central portion of the wire radially expands within the annular groove.

6. The electromechanical system according to claim 1, wherein the proximal housing assembly includes an inner housing including an annular lip and an outer wall, the annular groove defined between the annular lip and the outer wall, and a proximal end of the distal housing assembly abuts the annular lip.

7. The electromechanical system according to claim 6, wherein the central portion of the wire is annularly wound about the annular lip of the inner housing of the proximal housing assembly.

8. The electromechanical system according to claim 1, further comprising an end effector selectively connectable to the linkage of the shaft assembly, the end effector and the distal housing assembly configured to rotate together relative to the proximal housing assembly.

9. The electromechanical system according to claim 8, wherein the end effector is a linear surgical stapling end effector.

10. The electromechanical system according to claim 8, further comprising a surgical instrument selectively connectable to the elongate portion of the shaft assembly.

11. The electromechanical system according to claim 10, wherein the surgical instrument includes a motor.

12. The electromechanical system according to claim 10, wherein the distal portion of the wire is in electrical communication with the end effector and the proximal portion of the wire is in electrical communication with the surgical instrument, the wire configured to communicate information between the end effector and the surgical instrument.

13. The electromechanical system according to claim 1, wherein the shaft assembly includes a flexible portion.

14. The electromechanical system according to claim 1, wherein the gear is a rotation drive gear keyed to part of the distal housing assembly to rotate the distal housing assembly.

15. The electromechanical system according to claim 14, wherein the distal housing assembly includes a central cut-out including a slot extending therethrough, the slot configured to receive a shaft of the gear therein.

16. A linkage for operatively interconnecting an end effector to a surgical instrument, comprising:

a proximal housing assembly;

a distal housing assembly partially received within the proximal housing assembly and rotatable relative to the proximal housing assembly about a longitudinal axis;

a gear disposed within a recess defined in the proximal housing assembly; and a wire including a proximal portion coupled to the proximal housing assembly, a distal portion coupled to the distal housing assembly, and a central portion wound radially around the longitudinal axis within an annular groove defined between the proximal and distal housing assemblies, the central portion lying in a single plane with each successive winding of the wire disposed radially adjacent to an immediately prior winding.

17. The linkage according to claim 16, wherein the proximal portion of the wire is longitudinally fixed within the proximal housing assembly and the distal portion of the wire is longitudinally fixed within the distal housing assembly.

18. The linkage according to claim 16, wherein when the wire is disposed in a first configuration, prior to rotation of the distal housing assembly relative to the proximal housing assembly:

the proximal portion of the wire is disposed at a first radial distance from the longitudinal axis;

the distal portion of the wire is disposed at a second radial distance from the longitudinal axis; and the central portion of the wire is coiled within the annular groove between the first and second radial distances.

19. The linkage according to claim 16, wherein rotation of the distal housing assembly in a first direction relative to the proximal housing assembly causes the distal portion of the wire to rotate in the first direction such that the central portion of the wire radially contracts within the annular groove.

20. The linkage according to claim 19, wherein rotation of the distal housing assembly in a second direction relative to the proximal housing assembly causes the distal portion of the wire to rotate in the second direction such that the central portion of the wire radially expands within the annular groove.

* * * * *